United States Patent
Lee et al.

(10) Patent No.: US 9,151,682 B2
(45) Date of Patent: Oct. 6, 2015

(54) SENSOR FOR MEASURING AMOUNT OF HEAT GENERATED FROM CELLS USING ZWEIFACH-FUNG EFFECT AND METHOD FOR MANUFACTURING THE SAME

(75) Inventors: Sun Kyu Lee, Gwangju (KR); Sung Ki Nam, Gwangju (KR); Su Heon Jeong, Gwangju (KR); Jung Kyun Kim, Gwangju (KR); Do Kyun Woo, Gwangju (KR); Sung Yang, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 561 days.

(21) Appl. No.: 13/696,893

(22) PCT Filed: Dec. 8, 2010

(86) PCT No.: PCT/KR2010/008747
§ 371 (c)(1),
(2), (4) Date: Nov. 8, 2012

(87) PCT Pub. No.: WO2011/142518
PCT Pub. Date: Nov. 17, 2011

(65) Prior Publication Data
US 2013/0064265 A1      Mar. 14, 2013

(30) Foreign Application Priority Data

May 10, 2010    (KR) .................. 10-2010-0043588

(51) Int. Cl.
*G01K 17/00*        (2006.01)
*B01L 3/00*         (2006.01)
(Continued)

(52) U.S. Cl.
CPC ........... *G01K 17/00* (2013.01); *B01L 3/502761* (2013.01); *G01K 17/006* (2013.01);
(Continued)

(58) Field of Classification Search
CPC .............. G01K 17/00; G01N 25/4866; G01N 25/4846; C12Q 1/6827; C12Q 1/689
USPC ............ 374/120, 121, 179, 31; 435/6.12, 14; 702/130; 250/338.1
See application file for complete search history.

(56) References Cited

U.S. PATENT DOCUMENTS 8,043,814 B2 * 10/2011 Guilbeau ..................... 435/6.12

OTHER PUBLICATIONS

Yang et al., A microfluidic device for continuous, real time blood plasma separation, Lab Chip, 2006, 6, 871-880, 2006.*

*Primary Examiner* — Lisa Caputo
*Assistant Examiner* — Nathaniel T Woodward
(74) *Attorney, Agent, or Firm* — Nath, Goldberg & Meyer; Joshua B. Goldberg

(57) ABSTRACT

A sensor for measuring heat generated from cells, including a thermopile manufactured by surface-micromachining technology, and a microfluidic flow-channel structure for mixing cells with medium and dividing the mixture into cells and medium. Medium and cells are uniformly mixed using a micro-mixer. The mixture is separated into a medium microfluid and a cell microfluid using the Zweifach-Fung effect, after which signals measured in the two microfluids are amplified. The difference between the two signal values determines the amount of heat generated from the cells. The influence of noise caused by a change in external environment is eliminated. Convection heat dissipation caused by fluid flow is minimized. The sensor accurately measures the amount of heat generated from cells flowing in the microfluidic flow-channel. Diseases such as cancer are diagnosed using the difference between the measured amount of heat generated from cells and the standard amount of heat generated from normal cells.

19 Claims, 10 Drawing Sheets

(51) Int. Cl.
*G01N 25/20* (2006.01)
*G01N 25/48* (2006.01)
*C12Q 1/68* (2006.01)
(52) U.S. Cl.
CPC ........ *G01N 25/20* (2013.01); *B01L 2200/0652* (2013.01); *B01L 2200/147* (2013.01); *B01L 2300/0627* (2013.01); *B01L 2300/0645* (2013.01); *B01L 2300/087* (2013.01); *B01L 2300/0816* (2013.01); *B01L 2300/0883* (2013.01); *B01L 2300/1827* (2013.01); *C12Q 1/6827* (2013.01); *G01N 25/4846* (2013.01); *G01N 25/4866* (2013.01)

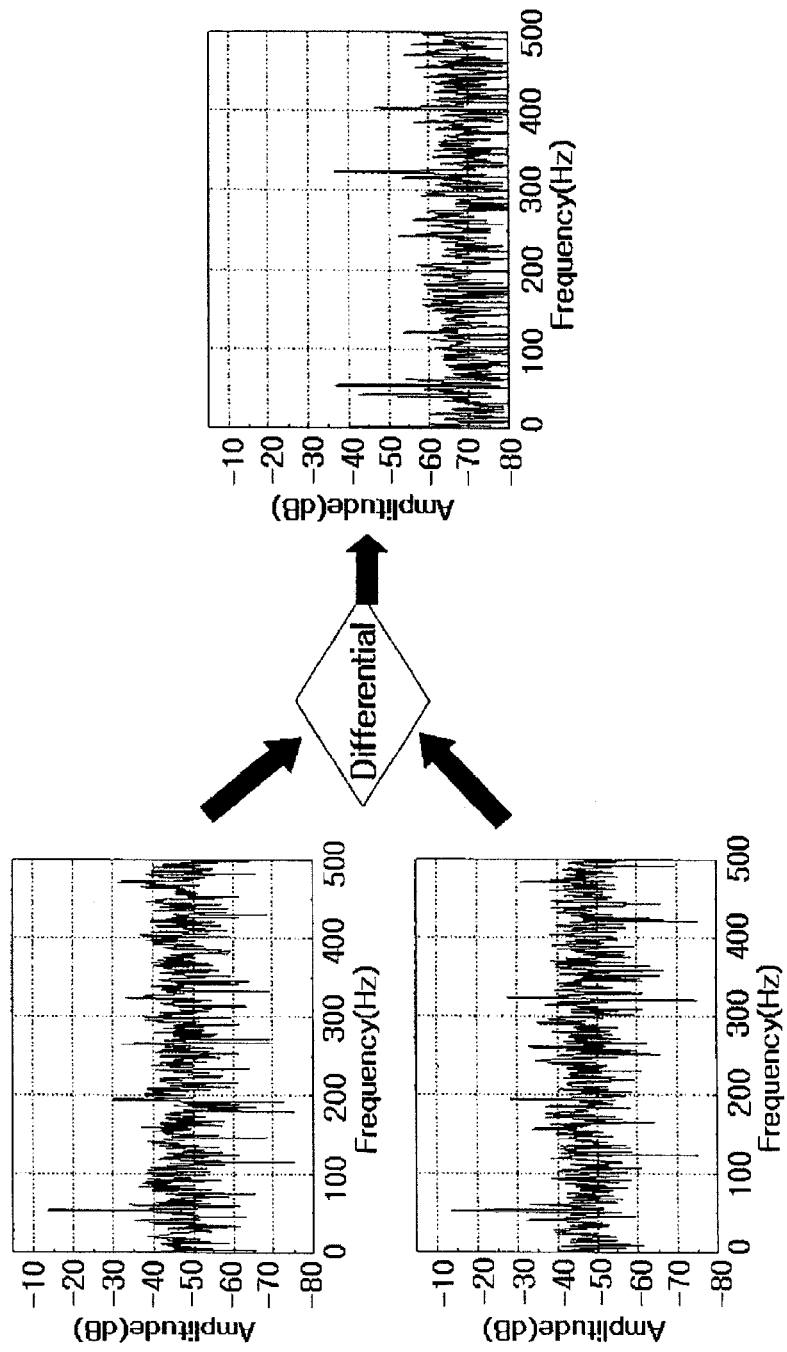

SENSOR FOR MEASURING AMOUNT OF HEAT GENERATED FROM CELLS USING ZWEIFACH-FUNG EFFECT AND METHOD FOR MANUFACTURING THE SAME

This is a National Phase Application filed under 35 U.S.C. 371 as a national stage of PCT/KR2010/008747 filed Dec. 8, 2010, and claims priority from Korean Application No. 10-2010-0043588, filed May 10, 2010, the content of each of which is hereby incorporated by reference in its entirety.

TECHNICAL FIELD

The present invention relates, in general, to a sensor for measuring the amount of heat generated from cells and a method for manufacturing the same, and more particularly to a sensor for measuring the amount of heat generated from cells, which can accurately measure the amount of heat generated from cells flowing in a microfluidic flow channel, and a method for manufacturing the same.

BACKGROUND ART

In recent years, methods of examining and diagnosing diseases based on the characteristics of cells have been developed. Thus, technology of rapidly and accurately measuring the characteristics of a small amount of cells has been required, and for this purpose, microfluidic devices have been introduced. Particularly, because the amount of heat generated from cancer cells and the like is about 1,000 times higher than that from normal cells, it is possible to early diagnose diseases such as cancer by measuring the amount of heat generated from cells. In addition, the activity of cells can be determined by measuring the amount of heat generated from tissue cells, and furthermore, the reaction rate and step can be determined by measuring the difference in the amount of generated heat between enzymes. Meanwhile, the amount of heat generated in cellular or enzymatic reactions is very low, and in order to accurately measure the amount of heat generation using a microfluidic device, the influence of an external environment should be removed and the influence of heat dissipation by convection during the flow of microfluids should be minimized. In addition, the amount of heat generated from cells should be measured in a state in which the cells are suspended in medium, so that the activity and survival time of the cells can be increased to ensure the accurate measurement of the amount of heat generated from the cells.

A sensor for measuring the amount of heat generated from cells according to the prior art is configured such that cells and medium are passed through a single microfluidic flow channel and a heat generation-measuring unit composed of a thermopile. In the prior art sensor for measuring the amount of heat generated from cells, medium and cells are injected through the single microfluidic flow channel. Thus, cells and medium are likely to be influenced by external noise caused by a change in atmospheric temperature, and convection heat dissipation in the heat generation-measuring unit by the flow of the medium occurs, making it difficult to accurately measure the amount of heat generated from the cells. Moreover, the convection heat transfer coefficient changes depending on the injection rates of medium and cells, and this change exerts an influence upon a signal for measuring the amount of heat generated. To overcome these shortcomings, the prior art sensor for measuring the amount of heat generated from cells requires a chamber, the temperature of which can be precisely controlled, and an ultra-low-flow rate fluid pump for controlling flow rate at a level of nl/min. In addition, to compensate for the temperature of the cold region of the thermopile, an assistant heater is required in addition to a main heater.

DISCLOSURE

Technical Problem

Accordingly, the present invention has been made keeping in mind the above-described problems occurring in the prior art, and an object of the present invention is to provide a sensor for measuring the amount of heat generated from cells, which can accurately measure the amount of heat generated from cells flowing in a microfluidic flow channel by eliminating the influence of external noise caused by a change in atmospheric temperature and minimizing convection heat dissipation caused by the flow of a fluid.

Another object of the present invention is to provide a method for manufacturing a sensor for measuring the amount of heat generated from cells according to the present invention.

Technical Solution

In order to accomplish the above objects, in one aspect, the present invention provides a sensor for measuring the amount of heat generated from cells, the sensor comprising: a thermopile manufactured by surface-micromachining technology, and a microfluidic flow channel structure for mixing cells with medium and separating the mixture into the cells and the medium. More specifically, the present invention provides a sensor for measuring the amount of heat generated from cells, the sensor comprising: a substrate; a membrane formed on at least one surface of the substrate; upper and lower thermopiles formed on the membrane; a passivation layer covering the exposed surfaces of the membrane, the upper thermopile and the lower thermopile; and a microfluidic flow channel structure formed on the passivation layer, the microfluidic flow channel structure comprising a medium inlet unit, a cell inlet unit being in fluidic communication with the medium inlet unit, a micro-mixer being in fluidic communication with the cell inlet unit, a cell-medium separation unit being in fluidic communication with the micro-mixer and composed of a first microfluidic flow channel and a second microfluidic flow channel, and a cell-medium outlet unit being in fluidic communication with the cell-medium separation unit. Herein, the ratio of the cross-sectional area between the first microfluidic flow channel and second microfluidic flow channel of the cell-medium separation unit is at least 4:1, and preferably at least 6:1, so that the first and second microfluidic flow channels have different flow rates such that the Zweifach-Fung effect sufficiently occur.

Also, the first microfluidic flow channel is located on the inner ends of any one of the upper thermopile and the lower thermopile, and the second microfluidic flow channel is located on the inner end of the other thermopile. The two thermopiles indirectly measure the amounts of heat generated from microfluids flowing the first microfluidic flow channel and the second microfluidic flow channel.

In addition, in order to establish the correlation between the amount of heat generated from cells and the output voltages of the thermopiles, the sensor for measuring the amount of heat generated from cells according to the present invention may further comprise a heater formed on the membrane, the heater being covered by the passivation layer and located adjacent to the inner end of the upper thermopile or the inner end of the lower thermopile.

Furthermore, in order to prevent heat, generated in the heater, from being reduced by dispersion and minimize a change in external temperature, which acts as noise on the microfluidic flows of cells and medium, the measurement sensor according to the present invention may further comprise a cavity formed in a predetermined region including a portion, which is opposite to the cell-medium separation unit and is defined in one surface of the substrate on which the upper thermopile, the lower thermopile, the passivation layer and the microfluidic flow channel structure are not formed. Particularly, when the substrate is a highly thermally conductive silicon substrate, the cavity significantly improves the performance of the sensor for measuring the amount of heat generated from cells.

In another aspect, the present invention provides a method for manufacturing a sensor for measuring the amount of heat generated from cells according to a preferred embodiment of the present invention, the method comprising the steps of: (a) forming a membrane on at least one surface of a substrate; (b) forming an upper thermopile and a lower thermopile on the membrane; (c) forming a passivation layer covering the exposed surfaces of the membrane, the upper thermopile and the lower thermopile; and (d) bonding onto the passivation layer a microfluidic flow channel structure open on one side, the microfluidic flow channel structure comprising a medium inlet unit, a cell inlet unit being in fluidic communication with the medium inlet unit, a micro-mixer being in fluidic communication with the cell inlet unit, a cell-medium separation unit being in fluidic communication with the micro-mixer and comprising a first microfluidic flow channel and a second microfluidic flow channel, which diverge from each other, and a cell-medium outlet unit being in fluidic communication with the cell-medium separation unit. Herein, the ratio of cross-sectional area between the first microfluidic flow channel and the second microfluidic flow channel in the cell-medium separation unit is at least 4:1, more preferably at least 6:1, so that the first microfluidic flow channel and the second microfluidic flow channel have different flow rates such that the Zweifach-Fung effect can be sufficiently used. In addition, the first microfluidic flow channel is located on the inner end of any one of the upper thermopile and the lower thermopile, and the second microfluidic flow channel is located on the inner end of the other thermopile. The two thermopiles indirectly measure the amounts of heat generated from microfluids which pass the first microfluidic flow channel and the second microfluidic flow channel.

In order to establish the correlation between the amount of heat generation and the output voltages of the thermopiles, step (b) of the method for manufacturing the measurement sensor according to the present invention further comprises forming on the membrane a heater adjacent to the inner end of the upper thermopile or the inner end of the lower thermopile, wherein the exposed surface of the heater is covered by the passivation layer in step (c).

In addition, in order to prevent heat, generated in the heater, from being reduced by dispersion and minimize a change in external temperature, which acts as noise the microfluidic flows of cells and medium, the method for manufacturing the measurement sensor according to the present invention may comprise step (e) of forming a cavity by etching a predetermined region including a portion, which is opposite to the cell-medium separation unit and is defined in one surface of the substrate on which the upper thermopile, the lower thermopile, the passivation layer and the microfluidic flow channel structure are not formed. Particularly, when the substrate is a highly thermally conductive silicon substrate, the cavity significantly improves the performance of the sensor for measuring the amount of heat generated from cells.

Advantageous Effects

In the sensor for measuring the amount of heat generated from cells according to the present invention, medium and cells are uniformly mixed with each other using a micro-mixer, and the mixture is separated into a medium microfluid and a cell microfluid using the Zweifach-Fung effect, after which two signals measured in the medium microfluid and the cell microfluid by the thermopiles are amplified, and the value of difference between the two signal values is used to determine the amount of heat generated from the cells. Thus, the influence of noise caused by a change in external environment can be eliminated, and convection heat dissipation caused by the flow of a fluid, that is, the decrease in heat generation caused by the flow of the medium, can be minimized. Thus, the inventive sensor for measuring the amount of heat generated from cells can accurately measure the amount of heat generated from cells flowing in the microfluidic flow channel, and diseases such as cancer can be diagnosed using the difference between the measured amount of heat generated from cells and the standard amount of heat generated from normal cells.

DESCRIPTION OF DRAWINGS

FIG. 10 shows a noise signal obtained from an upper thermopile (bottom left), a noise signal obtained from a lower thermopile (bottom right), and a noise signal corrected by a differential circuit (top), when the measurement sensor manufactured in Manufacture Example 1 was exposed to an external environment.

BEST MODE

Figure 1:
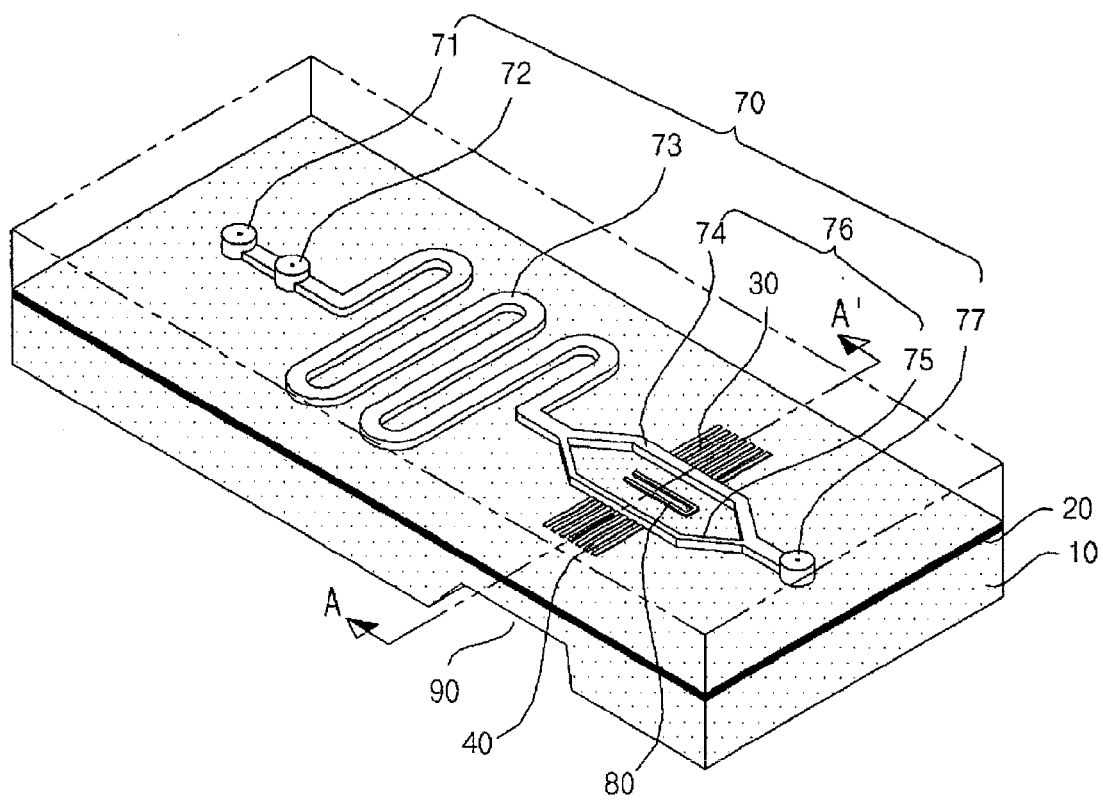
FIG. 1 is a perspective view of a sensor for measuring the amount of heat generated from cells according to a preferred embodiment of the present invention.

Hereinafter, preferred embodiments of the present invention will be described in detail with reference to the accompanying drawings. In reference numeral assigned to elements of respective drawings, it is noted that like elements are denoted by like reference numerals if possible although they are shown in different drawings. Also, in the following description, the detailed description of related known technology will be omitted when it may obscure the subject matter of the present invention. In addition, preferred embodiments of the present invention will be described, but those skilled in the art will appreciate that the technical idea of the present invention is not limited or restricted to these embodiments.

Figure 2:
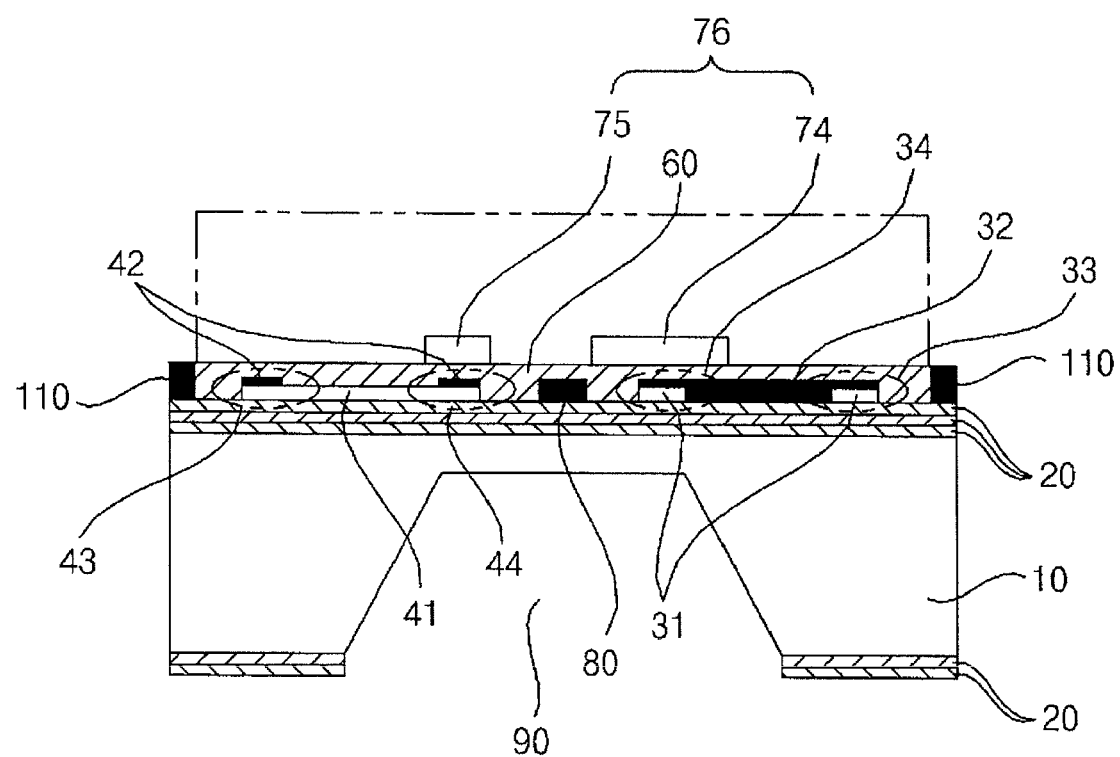
FIG. 2 is a cross-sectional view taken along line A-A' of FIG. 1.
Figure 3:
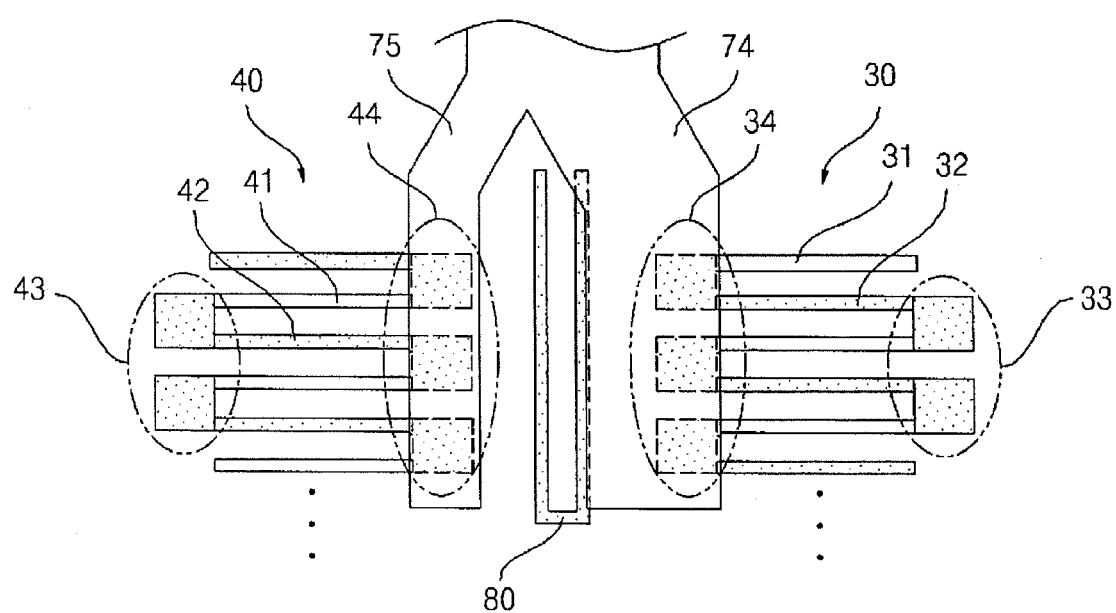
FIG. 3 is a partial top view of a sensor for measuring the amount of heat generated from cells according to a preferred embodiment of the present invention.
Figure 4:
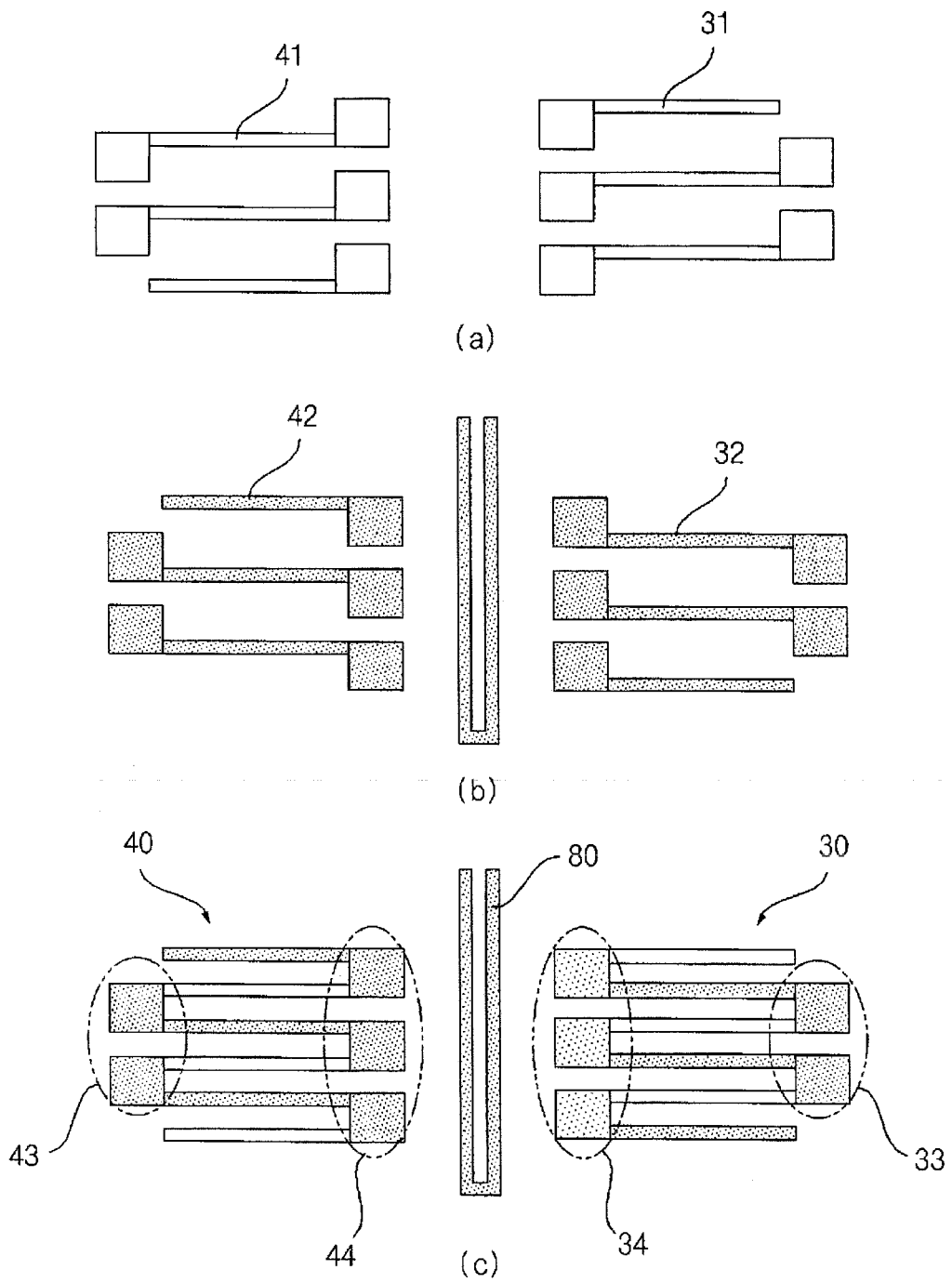
FIG. 4 schematically shows the structures of thermopile patterns adopted in a sensor for measuring the amount of heat generated from cells according to a preferred embodiment of the present invention.
Figure 5:
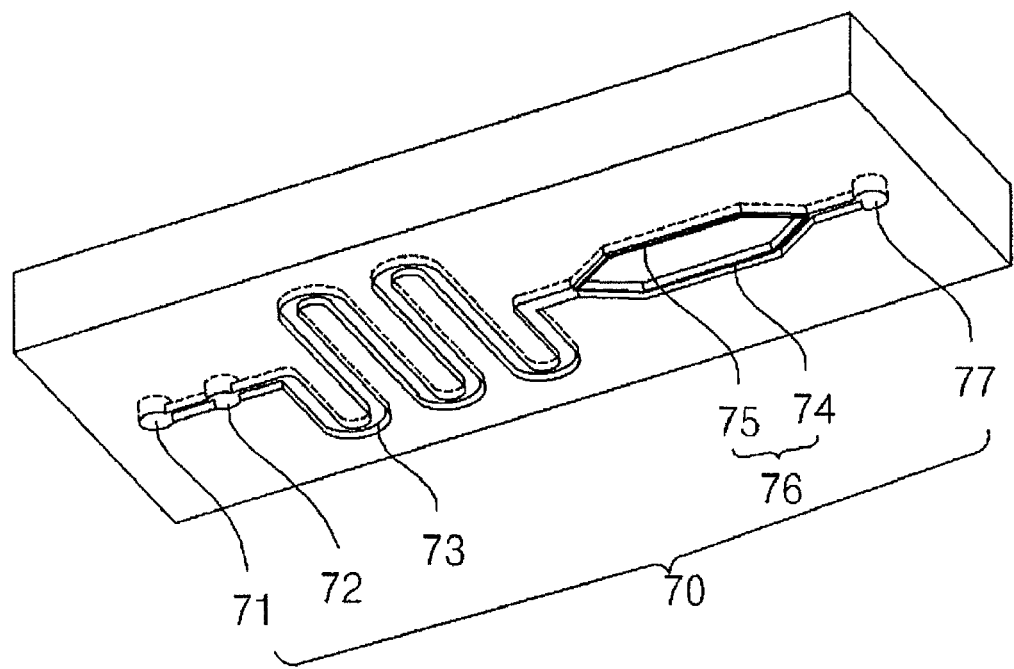
FIG. 5 is a perspective view of a microfluidic flow channel structure adopted in a sensor for measuring the amount of heat generated from cells according to a preferred embodiment of the present invention, before bonding to a passivation layer.
Figure 6:
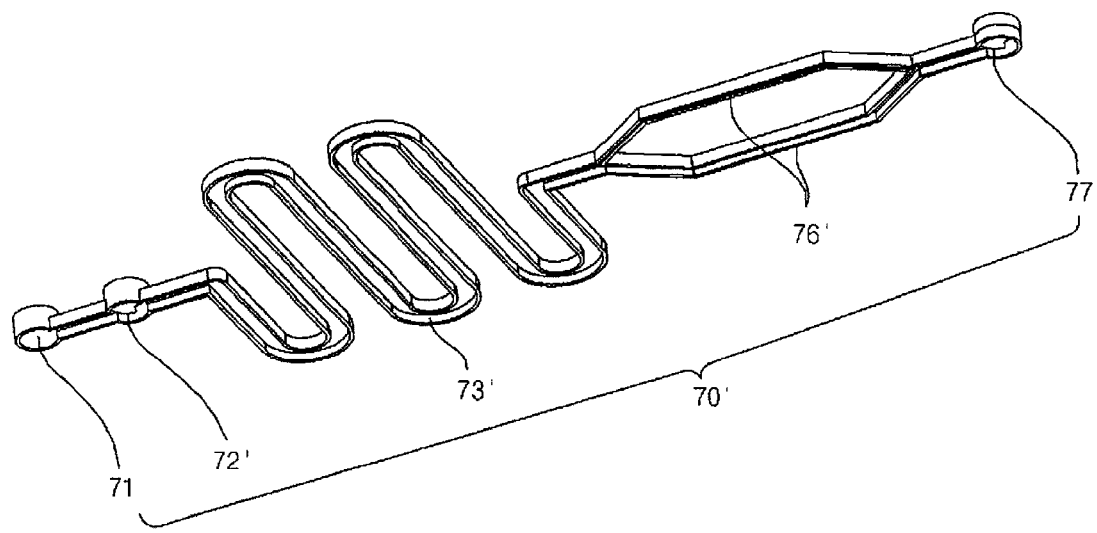
FIG. 6 is a perspective view of a microfluidic flow channel structure adopted in a sensor for measuring the amount of heat generated from cells according to another preferred embodiment of the present invention, before bonding to a passivation layer.

One aspect of the present invention is directed to a sensor for measuring the amount of heat generated from cells, which can accurately measure the amount of heat generated from cells flowing in a microfluidic flow channel by eliminating the influence of external noise caused by a change in atmospheric temperature and minimizing convection heat dissipation caused by the flow of a fluid. A sensor for measuring the amount of heat generated from cells according to a preferred embodiment of the present invention will now be described with reference to FIGS. 1 to 6. FIG. 1 is a perspective view of a sensor for measuring the amount of heat generated from cells according to a preferred embodiment of the present invention; FIG. 2 is a cross-sectional view taken along line A-A' of FIG. 1; FIG. 3 is a partial top view of a sensor for measuring the amount of heat generated from cells according to a preferred embodiment of the present invention; FIG. 4 schematically shows the pattern structure of a thermopile adopted in a sensor for measuring the amount of heat generated from cells according to a preferred embodiment of the present invention; FIG. 5 is a perspective view of a microfluidic flow channel structure adopted in a sensor for measuring the amount of heat generated from cells according to a preferred embodiment of the present invention, before adhesion to a passivation layer; and FIG. 6 is a perspective view of a microfluidic flow channel structure adopted in a sensor for measuring the amount of heat generated from cells according to another preferred embodiment of the present invention, before adhesion to a passivation layer.

As used herein, the term "cells" is meant to include all those that can be cultured, including animal cells, plant cells, human living cells, and microorganisms.

As shown in FIGS. 1 and 3, a sensor for measuring the amount of heat generated from cells according to a preferred embodiment of the present invention comprises: a substrate 10; a membrane 20 formed on at least one surface of the substrate; an upper thermopile 30 and a lower thermopile 40 formed on the membrane; a passivation layer 60 covering the exposed surfaces of the membrane, the upper thermopile and the lower thermopile; and a microfluidic flow channel structure 70 formed on the passivation layer, the microfluidic flow channel structure comprising a medium inlet unit 71, a cell inlet unit 72 being in fluidic communication with the medium inlet unit, a micro-mixer 73 being in fluidic communication with the cell inlet unit, a cell-medium separation unit 76 being in fluidic communication with the micro-mixer and composed of a first microfluidic flow channel 74 and a second microfluidic flow channel 75, which diverge from each other, and a cell-medium outlet unit 77 being in fluidic communication with the cell-medium separation unit.

In addition, the sensor for measuring the amount of heat generated from cells according to a preferred embodiment of the present invention may further comprise a heater 80 formed on the membrane, the heater being covered by the passivation layer and located adjacent to the inner end of the upper thermopile or the inner end of the lower thermopile. Moreover, the sensor for measuring the amount of heat generated from cells according to the present invention may further comprise a cavity 90 formed in a predetermined region including a portion, which is opposite to the cell-medium separation unit and is defined in one surface of the substrate on which the upper thermopile, the lower thermopile, the passivation layer and the microfluidic flow channel structure are not formed.

The substrate 10 is a base on which the thermopiles and the microfluidic flow channel structure are formed, and the substrate that is used in the present invention is not specifically limited, as long as it is generally used in the art. For example, the substrate may be a silicon substrate or a substrate made of a material similar thereto. Preferably, at least one surface of the substrate is polished.

The membrane 20 is a layer formed on at least one surface of the substrate and is preferably made of a low-stress insulating layer. The insulating layer may be made of a silicon oxide layer, a silicon nitride layer, a two-layer film of silicon oxide/silicon nitride, a two-layer film of silicon nitride/silicon oxide, a three-layer film of silicon oxide/silicon nitride/silicon oxide, or a three-layer film of silicon nitride/silicon oxide/silicon nitride. Among them, the insulating layer made of the three-layer film of silicon oxide/silicon nitride/silicon oxide comprises: a first insulating layer formed by depositing silicon dioxide ($SiO_2$) on one or both surfaces of the substrate to a thickness of about 0.5-1.0 μm, for example, 0.8 μm; a second insulating layer formed on the first insulating layer by depositing silicon nitride ($Si_3N_4$) on the first insulating layer to a thickness of about 0.2-0.6 μm, for example, 0.3 μm; and a third insulating layer formed on the second insulating layer by depositing silicon dioxide ($SiO_2$) to a thickness of about 0.3-1.0 μm, for example, 0.5 μm.

In a predetermined region on the membrane, two thermopiles, that is, the upper thermopile 30 and the lower thermopile 40 are formed. The two thermopiles preferably have a symmetrical structure with respect to the cell-medium separation unit as described below. Any one thermopile of the two thermopiles outputs a voltage corresponding to heat generated in the first microfluidic flow channel as described below, and the other thermopile outputs a voltage corresponding to heat generated in the second microfluidic flow channel as described below. In the upper thermopile and the lower thermopile, a plurality of thermocouples are connected alternately in series with each other in a hot region (formed by the cell-medium separation unit or the heater as described below) and a cold region (generally formed by the silicon substrate or the insulating layer). More specifically, a first thermoelectric material 31 or 41 and a second thermoelectric material 32 or 42, which are different from each other, are connected in series in series with each other in the hot region and the cold region. The upper thermopile and the lower thermopile have outer ends 33 and 43 and inner ends 34 and 44 in the regions in which the first thermoelectric material and the second thermoelectric material are connected in series in series with each other. The inner ends form a hot junction, and the outer ends form a cold junction. The material of the thermopiles is not specifically limited, and examples thereof include gold, nickel, polysilicon, aluminum and the like. In the sensor for measuring the amount of heat generated from cells according to a preferred embodiment of the present invention, the first thermoelectric material and the second thermoelectric material are gold and nickel, respectively, and as shown in FIG. 4, the upper thermopile and the lower thermopile are composed of a specific gold pattern, formed on the membrane, and a specific nickel pattern formed on the membrane. The hot junction and the cold junction, which are both ends of the upper thermopile and the lower thermopile, have a structure of nickel deposited on gold. Preferably, the sensor for measuring the amount of heat generated from cells according to a preferred embodiment of the present invention may further comprise an adhesion layer (not shown) formed between the specific gold pattern and the membrane and between the specific nickel pattern and the membrane. The material of the adhesion layer is chromium (Cr). Herein, chromium is deposited to a thickness of about 10-50 nm, and gold and nickel are deposited to a thickness of about 50-500 nm.

Preferably, the sensor for measuring the amount of heat generated from cells according to a preferred embodiment of the present invention may further comprise a heater 80 formed on the membrane and located adjacent to the inner end of the upper thermopile or the inner end of the lower thermopile. The heater is used to establish the correlation between the amount of heat generation and the output voltage of the thermopiles and is formed by depositing on the membrane the same material as used for the formation of the thermopiles. It is preferably formed between the upper thermopile and the lower thermopile, more preferably between the first microfluidic flow channel and the second microfluidic flow channel as described below. When a predetermined amount of heat is applied to the heater and the output voltage of the upper thermopile or the lower thermopile according to the application of the heat is measured, the correlation between the amount of heat applied to the heater and the output voltage of the thermopile can be established.

In addition, the sensor for measuring the amount of heat generated from cells according to a preferred embodiment of the present invention comprises a passivation layer covering the exposed surfaces of the membrane, the upper thermopile and the lower thermopile. In the case in which the sensor for measuring the amount of heat generated from cells according to a preferred embodiment of the present invention comprises the heater, the passivation layer covers the exposed surface of the heater. The passivation layer serves to prevent the thermopiles and the heater, which are made of thermoelectric materials, particularly metal patterns, from being oxidized or corroded by contact with air. The passivation layer is formed of the same silicon oxide or silicon nitride as that of the membrane, and in some cases, it may be formed of an insulating material such as polyimide. Specifically, in the case in which the passivation layer is formed of silicon oxide, the passivation layer is formed by depositing silicon dioxide ($SiO_2$) to a thickness of 0.3-1.2 µm, for example, 0.5 µm, so as to cover the exposed surfaces of the membrane, the thermopiles and the heater.

In addition, the sensor for measuring the amount of heat generated from cells according to a preferred embodiment of the present invention further comprises a contact pad 110 formed by removing a portion of the passivation layer, excluding the passivation layer portion formed on the upper thermopile, the lower thermopile and the heater. That is, the contact pad 110 is formed by removing the passivation layer portion formed on the membrane. The upper thermopile, the lower thermopile and the heater are electrically connected with the contact pad by metal wirings (not shown), and the contact pad is then electrically connected to external conductive wires (not shown).

In addition, the sensor for measuring the calorific value of cells according to a preferred embodiment of the present invention comprises a microfluidic flow channel structure 70 formed on the passivation layer. The microfluidic flow channel structure is formed by bonding onto the passivation layer a structure open on one side. As shown in FIG. 1, the microfluidic flow channel structure 70 comprises a medium inlet unit 71, a cell inlet unit 72, a micro-mixer 73, a cell-medium separation unit and a cell-medium outlet unit 77, which are sequentially placed in the lengthwise direction of the substrate and are in fluidic communication with each other. As used herein, the term "fluidic communication" means a structure through which a microfluid can continuously flow. The medium inlet unit 71 is an element having an inlet through which a medium required for cell culture can be introduced. The cell inlet unit 72 is an element having an inlet through which cells can be introduced, and it is in fluidic communication with the medium inlet unit so that the cells flow together with the medium introduced through the medium inlet unit. The micro-mixer 73 is an element for uniformly mixing cells and medium and is in fluidic communication with the cell inlet unit. The medium and cells passed through the cell inlet unit are passed through the micro-mixer while they are converted to a microfluid having a uniform cell concentration. The shape of the micro-mixer is not specifically limited, and as shown in FIG. 1, the micro-mixer may have a shape curved at both sides of the substrate, and in this case, the cells and the medium are uniformly mixed in the curved portions. The cell-medium separation unit 76 is an element for separating the mixture of the cells and the medium into a cell microfluid and a medium microfluid by the Zweifach-Fung effect and is in fluidic communication with the micro-mixer. The cell-medium separation unit is composed of a first microfluidic flow channel 74 and a second microfluidic flow channel 75, which diverge from the front end. The first microfluidic flow channel and the second microfluidic flow channel converge at the rear end of the cell-medium separation unit and are in fluidic communication with the cell-medium outlet unit. The first microfluidic flow channel is located on the inner end of any one of the upper thermopile and the lower thermopile, and the second microfluidic flow channel is located on the inner end of the other thermopile, and thus forming a hot region. The amounts of heat generation of the cell microfluid and the medium microfluid, which flow in the first and second microfluidic flow channels, are indirectly measured by the thermopiles. The Zweifach-Fung effect is a phenomenon in which cells that flow together with medium in one microfluidic flow channel tend to move toward a microfluidic flow channel having a larger amount of flow among two diverged microfluidic flow channels. This effect is caused by the difference in pressure between the channels and the difference in shear stress on the cell surface between the channels. The Zweifach-Fung effect is generally used to separate plasma from blood. In the present invention, the Zweifach-Fung effect is caused by the rate of flow in the first and second microfluidic flow channels. To cause the Zweifach-Fung effect, the ratio of cross-sectional area between the first microfluidic flow channel and the second microfluidic flow channel is 4:1 to 100:1, and preferably 6:1 to 35:1. When the ratio of cross-sectional area between the first microfluidic flow channel and the second microfluidic flow channel is 4:1, the Zweifach-Fung effect starts to occur, and when the ratio is 6:1, about 90% of cells are separated. If the ratio of cross-sectional area between the first microfluidic flow channel and the second microfluidic flow channel is more than 100:1, the cross-sectional area of the second microfluidic flow channel will be too small, and thus the cells and the medium will mostly be introduced into the first microfluidic flow channel to reduce the separation of the cells from the medium, and it will also be difficult to form the microfluidic flow channel structure. The material of the microfluidic flow channel structure 70 is not specifically limited, but is preferably a polymer resin in view of the easiness of formation, and specific examples thereof include polydimethylsiloxane (PDMS). The microfluidic flow channel structure can be framed by various methods, including extrusion molding, nanoimprint, or lithography, particularly photolithography or stereolithography. When the microfluidic flow channel structure 70 is formed by nanoimprint or lithography, as shown in FIG. 5, it is generally a structure having specific patterns corresponding to the medium inlet unit 71, the cell inlet unit 72, the micro-mixer 73, the cell-medium separation unit 76 and the cell-culture outlet unit 77, which are formed in a polymer resin layer of a specific thickness. Also, when the microfluidic flow channel structure is formed by extrusion molding using a mold, as shown in FIG. 6, the microfluidic flow channel structure 70' may comprise the medium inlet unit 71', the cell inlet unit 72', the micro-mixer 73', the cell-medium separation unit 76' and the cell-medium outlet unit 77', which are connected with each other.

In addition, the sensor for measuring the amount of heat from cells according to a preferred embodiment of the present invention may further comprise a cavity 90 formed in a predetermined region including a portion, which is opposite to the cell-medium separation unit and is defined in one surface of the substrate on which the upper thermopile, the lower thermopile, the passivation layer and the microfluidic flow channel structure are not formed. The cavity prevents heat, generated in the heater, from being reduced by dispersion, and minimizes the influence of a change in external temperature, which acts as noise on the microfluidic flow of the cells and the medium. Particularly, when the substrate is a highly thermally conductive silicon substrate, the cavity greatly improves the performance of the sensor for measuring the amount of heat generated from cells. As shown in FIG. 1, the cavity is preferably formed in the same direction as the direction of the thermoelectric material patterns formed on the upper and lower thermopiles, that is, the direction perpendicular to the lengthwise direction of the substrate. On the substrate surface portion opposite to the portion on which the cavity is formed, the cell-medium separation unit, the heater, the upper thermopile and the lower thermopile are located. The cavity is formed by wet-etching one surface of the substrate.

Figure 7:
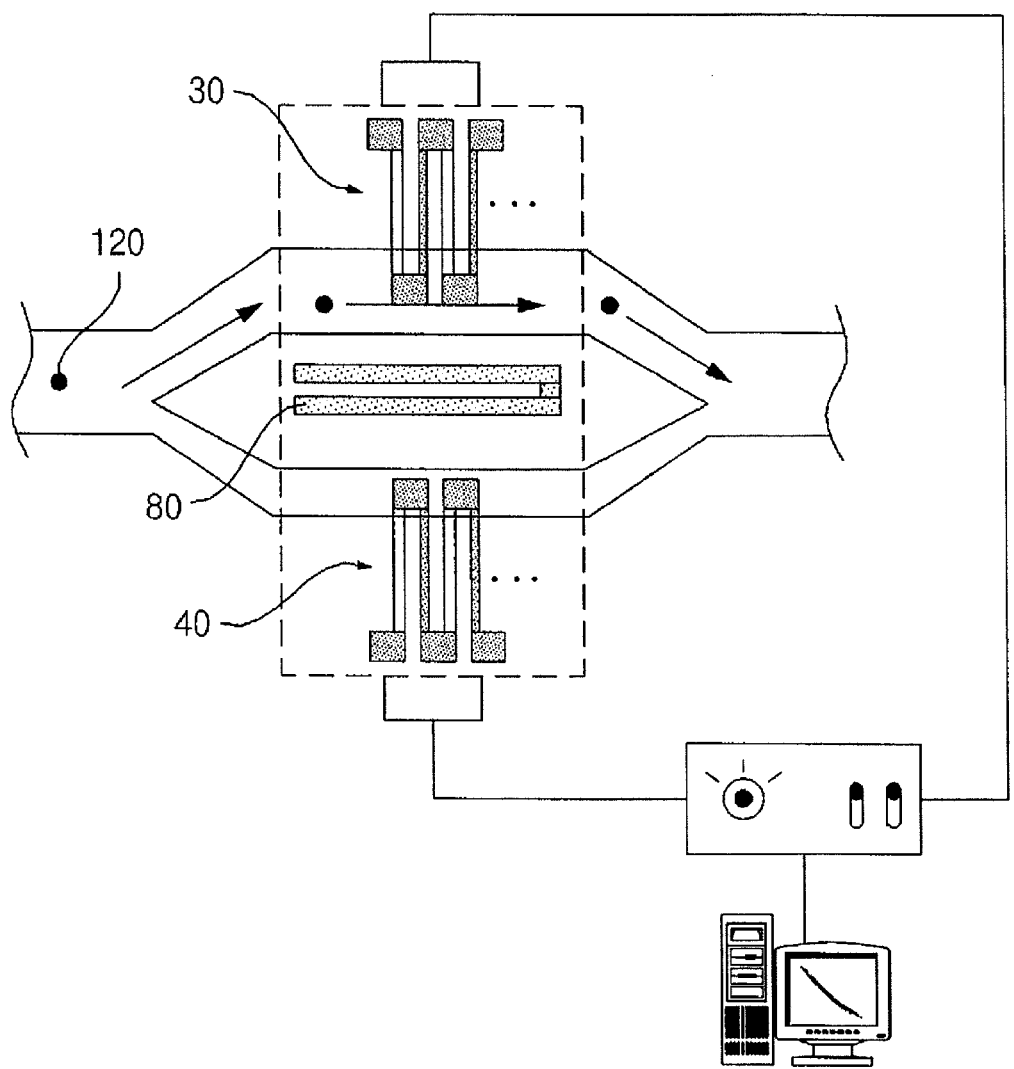
FIG. 7 schematically shows a process of measuring the amount of heat generated from cells using a measurement sensor according to a preferred embodiment of the present invention.

Hereinafter, a process of measuring the amount of heat generated from cells using the sensor for measuring the amount of heat generated from cells according to a preferred embodiment of the present invention will be described. FIG. 7 schematically shows a process of measuring the amount of heat generated from cells using the sensor for measuring the amount of heat generated from cells according to a preferred embodiment of the present invention. As shown in FIG. 7, a mixture of cells 120 and medium, uniformly mixed in the micro-mixer, is introduced into the cell-medium separation unit in which it is separated into a first microfluid, which comprises the majority of the cells, and a second microfluid consisting substantially of the medium. The first microfluid flows to the first microfluidic flow channel 74 receiving a relatively large amount of flow, and the second microfluid flows to the second microfluidic flow channel receiving a relatively small amount of flow. The amount of heat generated in the first microfluidic flow channel is output as a voltage value (V1) from the upper thermopile 30, and the amount of heat generated in the second microfluidic flow channel is output as a voltage value (V2) from the lower thermopile 40. FIG. 7 shows that the first microfluidic flow channel is located on the inner end of the upper thermopile, but the microfluidic flow channel structure may also be configured such that the first microfluidic flow channel is located on the inner end of the lower thermopile and the second microfluidic flow channel is located on the inner end of the upper thermopile. The output voltage values are amplified in amplifiers connected to the upper thermopile 30 and the lower thermopile 40 and are displayed as a V1-V2 value by the differential circuit of a terminal. The above displayed value of difference is a value from which the amount of heat generated from the medium has been subtracted, and thus when the amount of heat generated from cells is measured using the sensor according to the present invention, noise generated in medium by a change in external environment is minimized, and the effect of flow of medium on the decrease in the amount of heat generated is minimized. Also, because cells and medium are uniformly mixed in the micro-mixer before being separated in the cell-medium separation unit, noise caused by the non-uniformity of cells can be eliminated and a reliable value can be obtained. Comparison of the above value of difference with the value of difference measured for normal cells enables the diagnosis of diseases such as cancer. Also, when the correlation between the amount of heat generation and the output voltage from the thermopiles is established using the heater, the temperature according to the measured heat generation of cells can be determined. The output voltage of the thermopiles is a value corresponding to the difference in temperature between the cold region and the hot region, and thus when the temperature of the cold region is constant, the correlation between temperature and output voltage can be established by applying a predetermined amount of heat to the heater and measuring the temperature of the heater. Then, the output voltage obtained in the first microfluidic flow channel is converted to temperature (T1), and the output voltage obtained in the second microfluidic flow channel is converted to temperature (T2). The (T1-T2) value from which the temperature attributable to the medium has been subtracted is the temperature produced by the generation of heat from the cells.

Another aspect of the present invention is directed to a method for manufacturing the inventive sensor for measuring the amount of heat generated from cells. Hereinafter, the method for manufacturing the sensor for measuring the amount of heat generated from cells will be described in detail.

Figure 8:
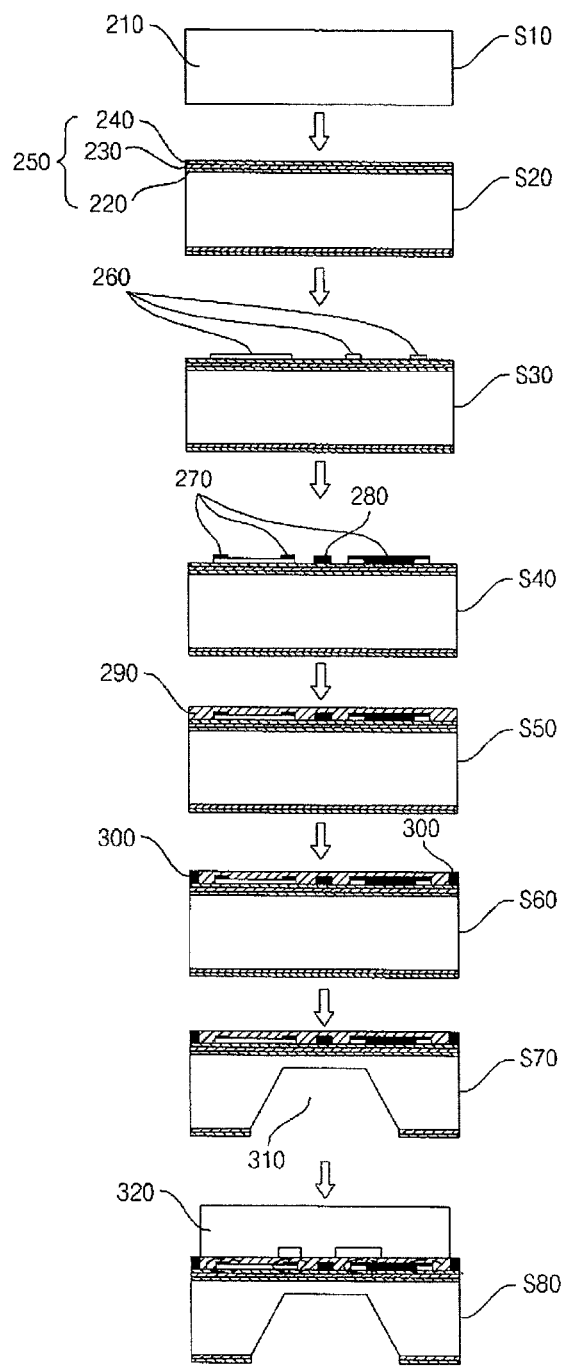
FIG. 8 schematically shows each step of a method for manufacturing a sensor for measuring the amount of heat generated from cells according to a preferred embodiment of the present invention.

FIG. 8 schematically shows each step of a method for manufacturing a sensor for measuring the amount of heat generated from cells according to a preferred embodiment of the present invention. As shown in FIG. 8, a method for manufacturing a sensor for measuring the amount of heat generated from cells according to a preferred embodiment of the present invention comprises the steps of: (a) forming a membrane on at least one surface of a substrate; (b) forming an upper thermopile and a lower thermopile on the membrane; (c) forming a passivation layer covering the exposed surfaces of the membrane, the upper thermopile and the lower thermopile; and (d) bonding onto the passivation layer a microfluidic flow channel structure open on one side, the microfluidic flow channel structure comprising a medium inlet unit, a cell inlet unit being in fluidic communication with the medium inlet unit, a micro-mixer being in fluidic communication with the cell inlet unit, a cell-medium separation unit being in fluidic communication with the micro-mixer and comprising a first microfluidic flow channel and a second microfluidic flow channel, which diverge from each other, and a cell-medium outlet unit being in fluidic communication with the cell-medium separation unit. Herein, the ratio of cross-sectional area between the first microfluidic flow channel and the second microfluidic flow channel is 4:1-100:1. Also, the first microfluidic flow channel is located on the inner end of any one of the upper thermopile and the lower thermopile, and the second microfluidic flow channel is located on the inner end of the other thermopile. In the method for manufacturing the sensor according to the present invention, step (b) further comprises forming a heater adjacent to the inner end of the upper thermopile or the inner end of the lower thermopile on the membrane in order to establish the amount of heat generation and the output voltage of the thermopile. The passivation layer in step (c) covers the exposed surface of the heater. Moreover, in order to prevent heat, generated from the heater, being reduced by dispersion and minimize a change in external temperature, which acts as noise on the microfluidic flows of cells and medium, the method for manufacturing the sensor according to the present invention may further comprise step (e) of forming a cavity by etching a predetermined region including a portion, which is opposite to the cell-medium separation unit and is defined in one surface of the substrate on which the upper thermopile, the lower thermopile, the passivation layer and the microfluidic flow channel structure are not formed. Particularly, when the substrate is a highly thermally conductive silicon substrate, the cavity greatly improves the performance of the sensor for measuring the amount of heat generated from cells.

More specifically, in the method for manufacturing the sensor for measuring the amount of heat generated from cells, a silicon substrate 210 polished on one or both surfaces is first prepared (S10). The polished silicon substrate is, for example, a p-type semiconductor substrate having a thickness of 500 μm.

Then, an insulating material is deposited on at least one surface of the silicon substrate 210 to form a membrane 250 (S20). The membrane is preferably composed of three insulating layers, and a method for forming the membrane comprises the steps of: depositing silicon oxide on at least one surface of the substrate to form a first insulating layer 220; depositing silicon nitride to form a second insulating layer 230; and depositing silicon oxide on the second insulating layer to form a third insulating layer 240. More specifically, silicon dioxide ($SiO_2$) are deposited on both surfaces of the silicon substrate to form a first insulating layer 220 having a thickness of 0.8 μm, and silicon nitride ($Si_3NH_4$) is deposited on the first insulating layer 220 to form a second insulating layer 230 having a thickness of 0.4 μm, and then silicon dioxide ($SiO_2$) is deposited on the second insulating layer 230 to form a third insulating layer 240 having a thickness of 0.9 μm. When the membrane is composed of a plurality of insulating layers formed of different materials, the insulating effect thereof is further improved. The insulating material is deposited by an LPCVD (low-pressure chemical vapor deposition) process or a PECVD (plasma-enhanced chemical vapor deposition) process. More preferably, the first insulating layer and the second insulating layer are formed by the LPCVD process, and the third insulating layer is formed by the PECVD or LPCVD process, but the scope of the present invention is not limited thereto. The LPCVD or PECVD process is a CVD (chemical vapor deposition) process of forming a thin film layer by inducing a chemical reaction between a gaseous compound and the silicon substrate 210. This chemical vapor deposition is mainly used in semiconductor manufacturing processes, because it can grow thin layers having various properties to the desired thicknesses, shows good step coverage and can easily control the composition of various compounds. The chemical vapor deposition process activates molecules using heat as an energy source, and as the energy source, plasma or light may also be used in addition to heat. Thus, it can be understand that the LPCVD process in the embodiment of the present invention is a chemical vapor deposition process utilizing heat energy, and the PECVD process is a chemical vapor deposition process utilizing plasma energy.

Then, an upper thermopile and a lower thermopile and optionally a heater are formed on the membrane. Specifically, a first thermoelectric material 260 is deposited on the membrane to form a first thermoelectric material pattern (S30). More specifically, photoresist (PR) is applied to the membrane to form a photoresist layer, and a negative patter consisting of a plurality of strips is formed therein. On the photoresist layer having the negative pattern formed therein, a first thermoelectric material is deposited using an electron beam. Herein, in order to enhance the adhesion of the first thermoelectric material, chromium (Cr) and the first thermoelectric material are preferably sequentially deposited. The deposited chromium serves as an adhesion layer. Then, the dummy photoresist layer is removed with a cleaner according to a lift-off method so that only the first thermoelectric material pattern remains. As the cleaner, acetone is used. When the first thermoelectric material is gold, chromium and gold are deposited to thicknesses of 20 nm and 100 nm, respectively.

After the first thermoelectric material pattern has been formed, the second thermoelectric material 270 is deposited so as to be connected alternately in series with the first thermoelectric material pattern, thereby forming an upper thermopile and a lower thermopile (S40). More specifically, the photoresist layer is formed on the membrane comprising the first thermoelectric material pattern consisting of a plurality of strips, and a negative pattern consisting of a plurality of strips is formed on the photoresist layer so as to be connected alternately in series with the first thermoelectric material pattern. On the photoresist layer, the second thermoelectric material is deposited using an electron beam. Preferably, chromium and the second thermoelectric material are sequentially deposited. Then, the dummy photoresist layer is removed using a cleaner according to a lift-off method so that only the first thermoelectric pattern and the second thermoplastic pattern remain. As the cleaner, acetone is used. When the second thermoelectric material is nickel, chromium and nickel are deposited to thicknesses of 20 nm and 200 nm, respectively. In addition, a heater 280 may further be formed between the upper thermopile and the lower thermopile by the second thermoelectric material.

Then, a passivation layer, which covers the exposed surfaces of the insulating layer, the upper thermopile and the lower thermopile, is formed (S50). When the heater is formed in the previous step, the passivation layer covers the exposed surface of the heater. For example, the passivation layer is formed by depositing silicon dioxide to a thickness of 0.5 to according to the PECVD process.

Then, a portion of the passivation layer, excluding the passivation layer portion formed on the upper thermopile, the lower thermopile and the heater, is removed. That is, the passivation layer portion formed on the membrane is removed, and a contact pad 300 is formed in the removed portion (S60). Specifically, the contact pad is formed by applying photoresist to the passivation layer to form a photoresist layer, forming a negative pattern to be etched, and etching a portion of the passivation layer by a dry etching process such as a plasma etching process.

Then, a cavity 310 is formed by etching a predetermined region of the substrate surface on which the upper thermopile, the lower thermopile, the passivation layer and the microfluidic flow channel structure are not formed (S70). The cavity is formed by a wet etching process such as an RIE (reactive ion etching) process. In the etching process, potassium hydroxide (KOH) is used as the etching solution, but is not limited thereto, and hydrochloric acid, nitric acid, sodium hydroxide, sulfuric acid, phosphoric acid, chromium oxide may also be used.

Then, a microfluidic flow channel structure 320 open on one side is bonded onto the passivation layer, thereby forming a microfluidic flow structure (S80). The microfluidic flow channel structure is formed of a polymer resin and is attached onto the passivation layer using a plasma bonding process.

Mode for Invention

Hereinafter, the present invention will be described in further detail with reference to examples. It is to be understood, however, that these examples are for illustrative purposes only and are not intended to limit the scope of the present invention.

MANUFACTURE EXAMPLE 1

Manufacture of Sensor for Measuring the Amount of Heat Generated from Cells

First, a p-type bare silicon wafer polished on both surfaces and having a thickness of 500 μm was prepared. On both surfaces of the prepared silicon wafer, silicon dioxide ($SiO_2$) was deposited to a thickness of about 0.8 μm by an LPCVD (low-pressure chemical vapor deposition) process to form a first insulating layer. On the first insulating layer on both surfaces of the silicon wafer, silicon nitride ($Si_3NH_4$) was deposited to a thickness of about 0.3 μm by an LPCVD (low-pressure chemical vapor deposition) process to form a second insulating layer. On the second insulating layer on both surfaces of the silicon wafer, silicon dioxide ($SiO_2$) was deposited to a thickness of about 0.5 μm by a PECVD (plasma-enhanced chemical vapor deposition) process to form a third insulating layer. Then, on the third insulating layer on the silicon wafer, photoresist (PR) was applied, and a negative pattern consisting of a plurality of strip was formed. Then, chromium was deposited to a thickness of 0.02 μm according to an electron beam evaporation to form an adhesive layer, and gold was deposited on the adhesion layer to a thickness of 0.1 μm, after which the patterned photoresist (PR) was removed with acetone, thereby forming a gold pattern. After the gold pattern has been formed, negative photoresist (PR) was applied to the first insulating layer on one surface of the silicon wafer, and a negative pattern consisting of a plurality of strands was formed so as to be connected alternatively in series with the gold pattern. Then, chromium was deposited to a thickness of 0.02 μm by an electron beam evaporation process to form an adhesion layer, and nickel was deposited on the adhesion layer to a thickness of 0.1 μm, after which the patterned photoresist (PR) was removed with acetone, thereby forming a nickel pattern connected 30 times alternately in series with the gold pattern. The gold pattern and the nickel pattern connected alternately in series with the gold pattern constitute thermopiles. The thermopiles consist of an upper thermopile and a lower thermopile, which are spaced from each other and symmetrical with respect to the silicon wafer. While the thermopiles were formed, a nickel pattern was formed between the upper thermopile and the lower thermopile, thereby forming a micro-heater. On the surface of the silicon wafer on which the thermopiles and the micro-heater were formed, silicon dioxide ($SiO_2$) was deposited to a thickness of about 1 μm by a PECVD (plasma-enhanced chemical vapor deposition) process to form a sacrificial layer. Then, a portion of the sacrificial layer was etched by a plasma dry etching process to form a contact pad region to be connected with a PCB by wire bonding. In addition, the other surface of the silicon wafer, on which the thermopiles and the micro-heater were not formed, was partially etched by a plasma dry etching process to expose the silicon wafer. Then, the exposed surface of the silicon wafer was etched to a depth of about 400 μm by an isotropic etching process at about 80° C., thereby forming a cavity having a size of about 660 μm×840 μm. After the cavity has been formed, a microfluidic flow channel structure was bonded by a plasma bonding process to the passivation layer of the silicon wafer on which the thermopiles and the micro-heater had been formed, thereby manufacturing a sensor for measuring the amount of heat generated from cells. Herein, the microfluidic flow channel structure was open on one side and comprised of specific channels corresponding to a medium inlet unit, a cell inlet unit, a micro-mixer, a cell-medium separation unit and a cell-medium outlet unit, which were formed in a polydimethylsiloxane (PDMS) polymer resin layer having a specific thickness. Herein, the cell-medium separation unit was in fluidic communication with the micro-mixer and composed of a first microfluidic flow channel and a second microfluidic flow channel, which diverged from each other. In addition, the ratio of cross-sectional area between the first microfluidic flow channel and the second microfluidic flow channel was 9:1. Furthermore, the first microfluidic flow channel was located on the inner end of the upper thermopile, and the second microfluidic flow channel was located on the inner end of the lower thermopile.

TEST EXAMPLE 1

Microbead Test

Figure 9:
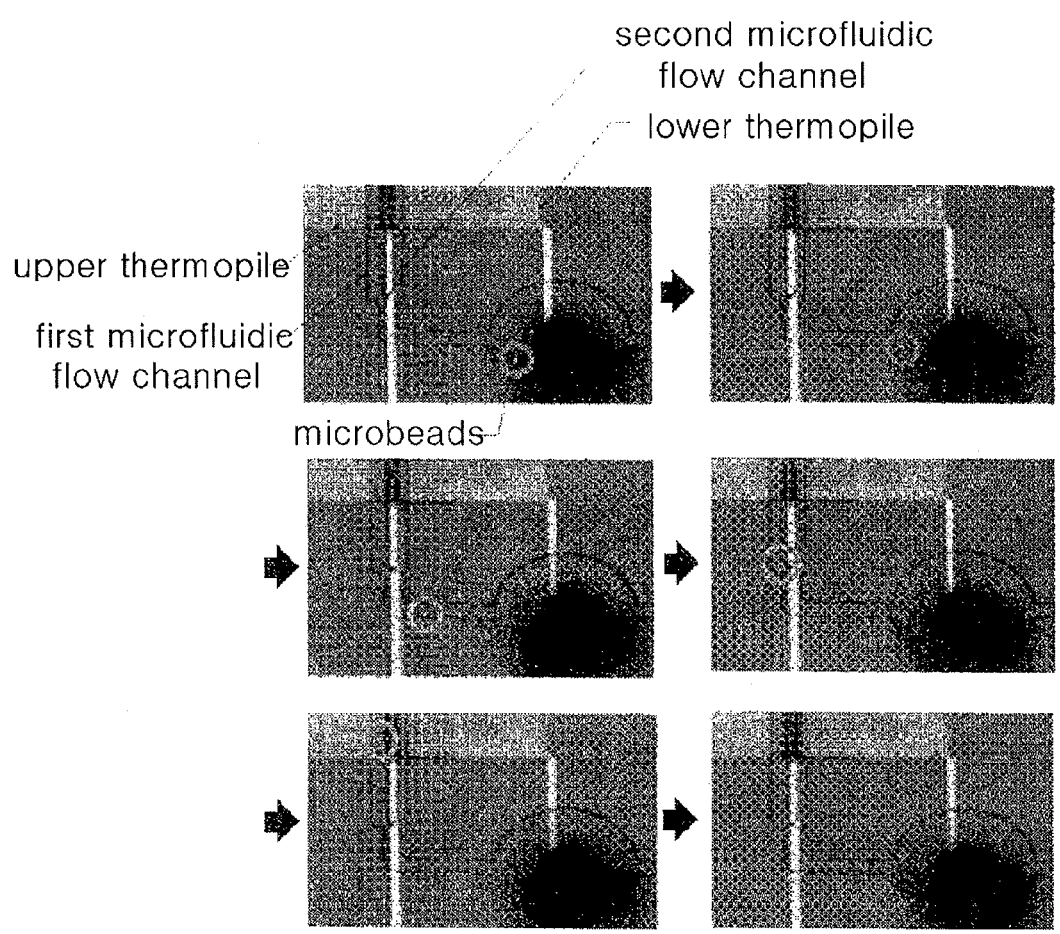
FIG. 9 shows the path of flow of microbeads introduced into the sensor for measuring the amount of heat generated from cells, manufactured in Manufacture Example 1.

Distilled water in place of medium was introduced into the medium inlet unit of the sensor for measuring the amount of heat generated from cells, manufactured in Manufacture Example 1, and microbeads having a particle diameter of about 16 were introduced into the cell inlet unit, thereby testing the Zweifach-Fung effect. FIG. 9 shows the path of flow of the microbeads introduced into the sensor for measuring the amount of heat generated from cells, manufactured in Manufacture Example 1. As shown in FIG. 9, the microbeads moved from the Y-shaped bifurcation point to the first microfluidic flow channel having a larger cross-sectional area.

TEST EXAMPLE 2

Effect of Differential Circuit on Decrease in Noise

An amplified was connected to each of the upper thermopile and lower thermopile of the sensor for measuring the amount of heat generated from cells, manufactured in Manufacture Example 1, and a differential circuit for correcting signals produced from the two amplifiers was constructed. Then, the sensor was exposed to an external environment, and a noise signal (decibel, (dB)) was obtained from each of the upper thermopile and the lower thermopile. The two noise signals were corrected by the differential circuit. FIG. 10 shows a noise signal obtained from the upper thermopile (bottom left), a noise signal obtained from the lower thermopile (bottom right), and a noise signal corrected by the differential circuit (top), when the sensor manufactured in Manufacture Example 1 was exposed to an external environment. As shown in FIG. 10, the signal obtained from each of the thermopiles showed a high noise level of about −45 dB, but the noise level of the signal corrected by the differential circuit significantly decreased to about −70 dB.

The above-described embodiments of the present invention have been disclosed for illustrative purposes only, and those skilled in the art will appreciate that various modifications, additions and substitutions are possible, without departing from the essential characteristics of the present invention. Therefore, the embodiments disclosed in the present invention and the accompanying drawings are not intended to limit the scope of the invention and are for illustrative purposes. It is to be understood that the scope of the present invention should be determined by the appended claims and that all technical ideas equivalents to the claims fall within the scope of the present invention.

The invention claimed is:

1. A sensor for measuring an amount of heat generated from cells, the sensor comprising:
   a substrate;
   a membrane formed on at least one surface of the substrate;
   upper and lower thermopiles formed on the membrane;
   a passivation layer covering exposed surfaces of the membrane, the upper thermopile and the lower thermopile; and
   a microfluidic flow channel structure formed on the passivation layer, the microfluidic flow channel structure comprising a medium inlet unit, a cell inlet unit being in fluidic communication with the medium inlet unit, a micro-mixer being in fluidic communication with the cell inlet unit, a cell-medium separation unit being in fluidic communication with the micro-mixer and composed of a first microfluidic flow channel and a second microfluidic flow channel, and a cell-medium outlet unit being in fluidic communication with the cell-medium separation unit,
   wherein a ratio of cross-sectional area between the first microfluidic flow channel and second microfluidic flow channel of the cell-medium separation unit is 4:1 to 100:1, the first microfluidic flow channel is located on an inner end of any one of the upper thermopile and the lower thermopile, and the second microfluidic flow channel is located on an inner end of the remaining thermopile.

2. The sensor of claim 1, further comprising a heater formed on the membrane, the heater being covered by the passivation layer and located adjacent to the inner end of the upper thermopile or the inner end of the lower thermopile.

3. The sensor of claim 2, further comprising a cavity formed in a predetermined region including a portion, which is opposite to the cell-medium separation unit and is defined in one surface of the substrate on which the upper thermopile, the lower thermopile, the passivation layer and the microfluidic flow channel structure are not formed.

4. The sensor of claim 1, wherein the membrane is an insulating layer.

5. The sensor of claim 4, wherein the insulating layer includes a silicon oxide layer, a silicon nitride layer, a two-layer film of silicon oxide/silicon nitride, a two-layer film of silicon nitride/silicon oxide, a three-layer film of silicon oxide/silicon nitride/silicon oxide, or a three-layer film of silicon nitride/silicon oxide/silicon nitride.

6. The sensor of claim 1, wherein the upper and lower thermopiles are composed of a plurality of thermocouples which are connected alternately in series with each other in a hot region and a cold region, the inner ends of the upper thermopile and the lower thermopile form a hot junction, and outer ends of the upper thermopile and the lower thermopile form a cold junction.

7. The sensor of claim 6, wherein each of the thermocouples is composed of a first thermoelectric material and a second thermoelectric material, which are mutually different and connected alternately in series with each other, in which the first thermoelectric material and the second thermoelectric material are gold and nickel, respectively.

8. The sensor of claim 1, wherein the microfluidic flow channel structure is formed of a polymer resin.

9. The sensor of claim 8, wherein the polymer resin is polydimethylsiloxane (PDMS).

10. The sensor of claim 1, wherein the ratio of cross-sectional area between the first microfluidic flow channel and second microfluidic flow channel of the cell-medium separation unit is 6:1 to 35:1.

11. A method for manufacturing a sensor for measuring an amount of heat generated from cells, the method comprising:
   (a) forming a membrane on at least one surface of a substrate;
   (b) forming an upper thermopile and a lower thermopile on the membrane;
   (c) forming a passivation layer covering exposed surfaces of the membrane, the upper thermopile and the lower thermopile; and
   (d) bonding a microfluidic flow channel structure, one side of which is open, onto the passivation layer, the microfluidic flow channel structure comprising a medium inlet unit, a cell inlet unit being in fluidic communication with the medium inlet unit, a micro-mixer being in fluidic communication with the cell inlet unit, a cell-medium separation unit being in fluidic communication with the micro-mixer and comprising a first microfluidic flow channel and a second microfluidic flow channel, which diverge from each other, and a cell-medium outlet unit being in fluidic communication with the cell-medium separation unit,
   wherein a ratio of cross-sectional area between the first microfluidic flow channel and second microfluidic flow channel of the cell-medium separation unit is 4:1 to 100:1, the first microfluidic flow channel is located on an inner end of any one of the upper thermopile and the lower thermopile, and the second microfluidic flow channel is located on an inner end of the remaining thermopile.

12. The method of claim 11, wherein step (b) further comprises forming a heater on the membrane in adjacent to the inner end of the upper thermopile or the inner end of the lower thermopile, and an exposed surface of the heater is covered with the passivation layer in step (c).

13. The method of claim 12, further comprising:
   (e) forming a cavity by etching a predetermined region including a portion, which is opposite to the cell-medium separation unit and is defined in one surface of the substrate on which the upper thermopile, the lower thermopile, the passivation layer and the microfluidic flow channel structure are not formed.

14. The method of claim 13, wherein the etching in step (e) is carried out by a wet-etching process using a potassium hydroxide etchant.

15. The method of claim 11, wherein the ratio of cross-sectional area between the first microfluidic flow channel and second microfluidic flow channel of the cell-medium separation unit is 6:1 to 35:1.

16. The method of claim 11, wherein step (a) comprises:
   (a1) depositing silicon oxide on at least one surface of the substrate to form a first insulating layer;
   (a2) depositing silicon nitride on the first insulating layer to form a second insulating layer; and
   (a3) depositing silicon oxide on the second insulating layer to form a third insulating layer.

17. The method of claim 11, wherein step (b) comprises:
   (b1) depositing a first thermoelectric material on the membrane to form a first thermoelectric material pattern; and
   (b2) depositing a second thermoelectric material such that the second thermoelectric material is connected alternately in series with the first thermoelectric material pattern, thereby forming the upper thermopile and the lower thermopile.

18. The method of claim 17, wherein step (b1) comprises:
(b11) forming a photoresist layer on the membrane and forming a negative pattern consisting of a plurality of strands;
(b12) sequentially depositing chromium and the first thermoelectric material on the photoresist layer; and
(b13) removing a dummy photoresist layer to leave only a pattern of a first thermoelectric material, and
step (b2) comprises:
(b21) forming a photoresist layer on the membrane comprising the first thermoelectric material pattern consisting of a plurality of strands, and forming a negative pattern of a plurality of strands so as to be connected alternately in series with the first thermoelectric material pattern;
(b22) sequentially depositing chromium and a second thermoelectric material on the photoresist layer; and
(b23) removing a dummy photoresist layer to leave only a pattern of the first thermoelectric material and a pattern of the second thermoelectric material.

19. The method of claim 18, wherein the first thermoelectric material and the second thermoelectric material are gold and nickel, respectively.

* * * * *